United States Patent [19]

Godin

[11] Patent Number: 4,491,786

[45] Date of Patent: Jan. 1, 1985

[54] TRANSDUCER FOR MEASURING PARTICLES SUSPENDED IN A FLUID

[75] Inventor: Thomas J. Godin, Ft. Lauderdale, Fla.

[73] Assignee: Coulter Electronics, Inc., Hialeah, Fla.

[21] Appl. No.: 339,809

[22] Filed: Jan. 15, 1982

Related U.S. Application Data

[63] Continuation of Ser. No. 942,033, Sep. 13, 1978, abandoned.

[51] Int. Cl.³ .................. G01N 15/02; G01N 27/07
[52] U.S. Cl. .................................. 324/71.1; 324/71.4
[58] Field of Search ........................... 324/71.1, 71.4

[56] References Cited

U.S. PATENT DOCUMENTS

| Re. 28,558 | 9/1975 | Hogg | 324/71.1 |
|---|---|---|---|
| 3,588,053 | 6/1971 | Rothermel | |
| 3,902,115 | 8/1975 | Hogg et al. | 324/71.1 |
| 3,982,182 | 9/1976 | Hogg | 324/71.1 |
| 4,001,678 | 1/1977 | Berg | 324/71.1 |
| 4,014,611 | 3/1977 | Simpson et al. | 324/71.4 X |
| 4,136,970 | 1/1979 | Cabrera et al. | |
| 4,140,966 | 2/1979 | Godin et al. | 324/71.1 |
| 4,290,011 | 9/1981 | Berg et al. | 324/71.1 |

*Primary Examiner*—Gerard R. Strecker
*Attorney, Agent, or Firm*—Gerald R. Hibnick

[57] ABSTRACT

A transducer for measuring particles suspended in a fluid is disclosed. The transducer includes an elongated tubular member having a particle-free fluid conducting channel and an aperture for permitting the flow of a particle containing fluid into the fluid conducting channel. The size of the particles is measured by measuring the impedance variation of the particle containing fluid as it passes through the aperture. Spurious variations of the impedance caused by reentry of the particles into the region about the aperture is prevented by spacing the wall of the channel opposite the aperture so that the particle containing fluid impinges thereon after passing through the aperture and so that the particle-free fluid transports the particles away from the aperture before the particles reenter the region about the aperture.

8 Claims, 4 Drawing Figures

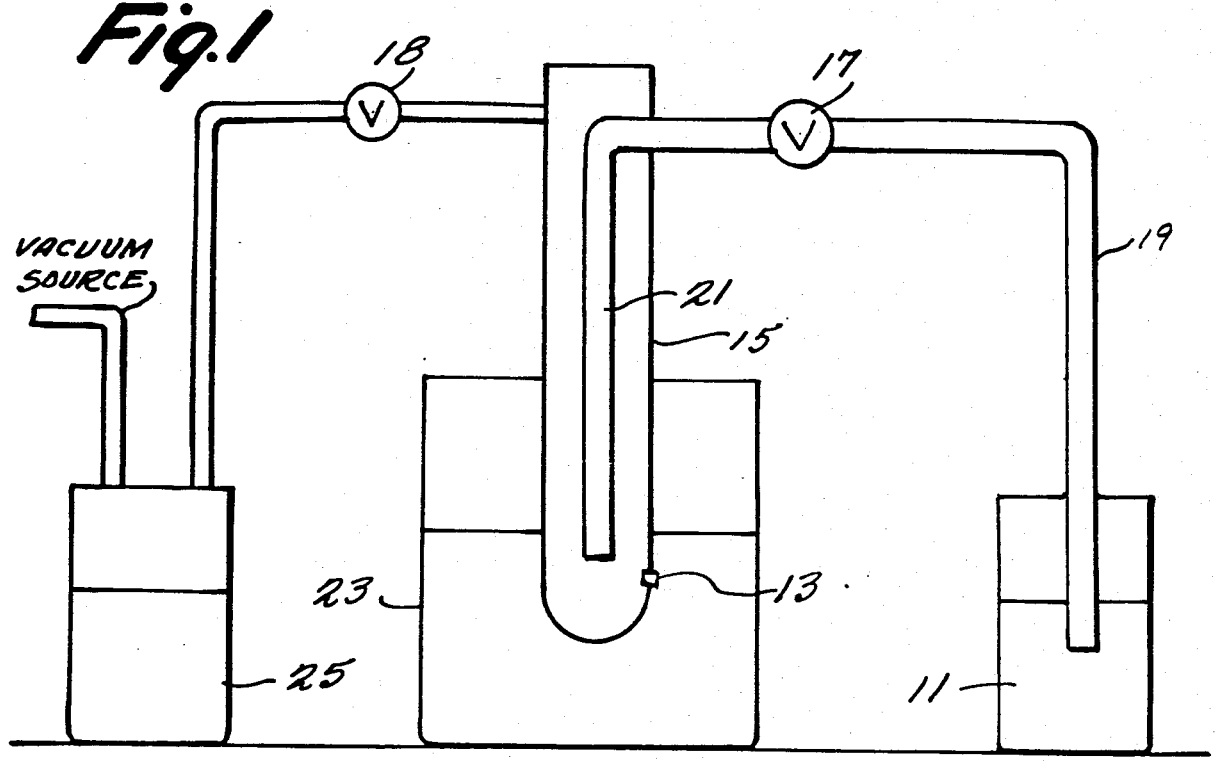
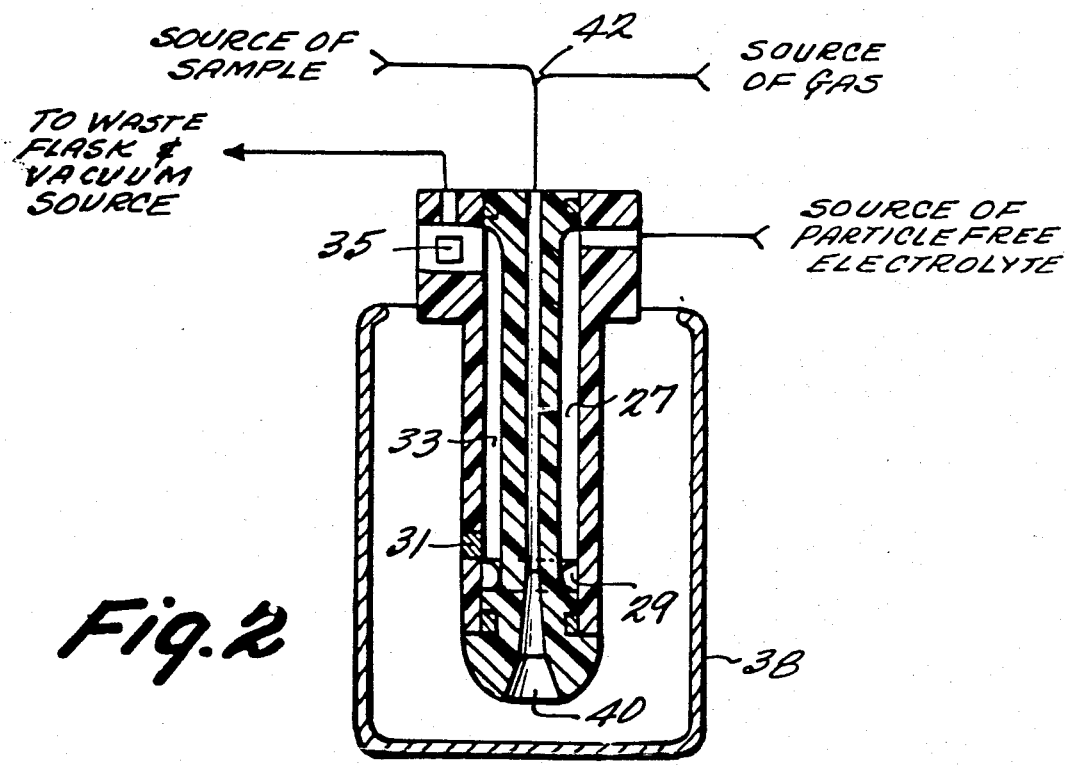

TRANSDUCER FOR MEASURING PARTICLES SUSPENDED IN A FLUID

This application is a continuation of application Ser. No. 942,033, filed Sept. 13, 1978, now abandoned.

BACKGROUND OF THE INVENTION

This invention relates to a transducer utilized to measure particles or cells suspended in a fluid.

A number of different techniques have been developed for measuring or counting particles in a fluid. An early technique was developed wherein the particle containing fluid was passed through an aperture having a relatively small diameter. An electric current was conducted through the aperture and the impedance variations of the particle containing fluid in the aperture was measured. The presence of a particle altered the impedance characteristics of the current conducting path through the aperture and therefore gave an indication of the size of a particle. Under certain circumstances, if the particle size was known, other characteristics of the particle could be deduced. A detailed description of this measuring technique is presented in Coulter U.S. Pat. No. 2,656,508 and Coulter et al. U.S. Pat. No. 2,869,078.

After this technique was developed, it was recognized that as the particles in the fluid suspension pass through the aperture, the particles flow or whirl back into the immediate vicinity of the downstream end of the aperture to cause another variation in the impedance of the current path. This impedance variation is caused by the particles entering an area of relatively high current density proximate the aperture. This gave rise to spurious or erroneous readings which were unacceptable. Various techniques have been developed to overcome this problem none of which are completely satisfactory. One such technique is illustrated in Hogg U.S. Pat. No. 3,299,354 wherein an aperture tube is provided which has two chambers. The first chamber has an aperture for permitting the passage of the particle containing fluid therethrough. The second chamber has an open end or orifice terminating at a point very closely spaced from and in alignment with the downstream end of the aperture in the first chamber. The purpose of this structure is to separate the electrical and mechanical effects of the particles passing through the aperture. This development has the drawback, however, of generating eddy currents of fluid in the aperture tube at the downstream end of the first chamber and these eddy currents swirled into the orifice of the second chamber. This caused the particles to swirl back into the high current density area proximate the aperture to thereby generate error in the testing of the particles in the fluid suspension.

In order to overcome this, a system was developed as disclosed in Hogg U.S. Pat. No. Re. 28,558 wherein substantially the same tubular structure was utilized as in the earlier Hogg '354 patent. However, a pump was provided to generate a continuous flow of the particle containing fluid in order to draw the particle containing fluid through the aperture and through the orifice of the second chamber so that the particles were continuously transported away from the high current density zone or region proximate the aperture. As acknowledged in a later patent, i.e., Hogg et al. U.S. Pat. No. 3,902,115, the structure disclosed in U.S. Pat. No. Re. 28,558 was relatively fragile and cumbersome and difficult to manufacture with the tolerances required. In addition, the flow velocity required in order to sweep out particles after they passed through the aperture had to be extremely high and, therefore, in order for the aperture to work, either a very minute restriction area downstream of the aperture between the aperture and the second chamber was required or exceedingly large quantities of fluid had to be pumped through the aperture tube.

To overcome this problem, and others associated with this structure, Hogg et al. developed, as illustrated in U.S. Pat. No. 3,902,115, an aperture tube structure wherein an electrolyte is pumped through one chamber of an aperture tube and into a second chamber either through an orifice or past a restriction which is positioned in very close proximity to the aperture. The orifice or restriction serves as a means for generating a high sweep velocity to cause all particles proximate the aperture to be drawn away from the high current density or spurious signal zone and into the second chamber. As in the case of the '115 patent, exceedingly high sweep velocities are required in order to make the tube operate as intended and, therefore, structurally a very minute restriction downstream of the aperture is required. Such a restriction is not only difficult to form structurally because of the tolerances required, but also generates a high series electrical resistance to the current flow through the aperture area. Further, this arrangement requires a relatively large flow of electrolyte for clearing the particles from the spurious signal zone near the aperture.

Another technique, as illustrated in simplified form in FIG. 1, uses the basic apparatus disclosed in Coulter et al. U.S. Pat. No. 2,869,078. As illustrated, a flask 11 contains an electrolyte which is used to wash or remove particles from the spurious signal zone proximate the aperture 13 of an aperture tube 15. A stopcock 17 is partially opened and a vacuum which is established in the aperture tube 15 via control valve 18 draws the electrolyte from flask 11 through conduit 19, the stopcock 17, and through tube 21 into the aperture tube 15. The particle containing fluid is located in a container 23 and this fluid is drawn into the aperture tube 15 through aperture 13. The electrolyte from flask 11 serves to dilute and wash away the particles passing through the aperture 13 and into a waste flask 25. The electrolyte has the effect of diluting the area behind the aperture 13 thereby reducing the probability of cells or particles reentering the spurious signal zone proximate the aperture. This technique measurably reduces the number of spurious signals generated but requires a substantial amount of electrolyte and, in addition, does not completely eliminate spurious signals.

It, therefore, is an important objective of the present invention to provide a structurally simplified transducer for measuring particles suspended in a fluid medium wherein error due to the recirculation of the particles in a region proximate an aperture in an aperture tube is minimized.

SUMMARY OF THE INVENTION

Accordingly, the present invention relates to an improved transducer for measuring particles suspended in a fluid wherein the transducer includes a fluid conducting channel for permitting the flow of a substantially particle-free electrolyte therethrough and having an aperture for permitting the passage of a particle containing fluid into the fluid conducting channel. The variations of impedance of the particle containing fluid in the aperture is measured to thereby determine the size and number of the particles. A region in the channel proximate to and downstream of the aperture is established wherein when the particles recirculate into this region after passing through the aperture, spurious impedance variations are generated. In order to eliminate this, the wall of the channel opposite the aperture is sufficiently spaced from the aperture to permit particles in the particle containing fluid to move past this region and to impinge upon the wall to thereby diffuse the particles. The electrolyte flowing through the channel transports the particles away from the region before the particles have a chance to recirculate in the region proximate the aperture.

The transducer, also, includes a particle containing fluid admitting channel through which the particle containing fluid flows into a container and about the transducer. After the fluid has passed into the container through the fluid admitting channel, air or any other suitable gas is controllably forced through the channel and into the container for the dual purpose of clearing the channel of the fluid and mixing the particle containing fluid so that it is maintained homogeneous.

BRIEF DESCRIPTION OF THE DRAWINGS

Other objects, features and advantages of the invention will become more fully apparent from the following detailed description of the preferred embodiment of the invention, the appended claims and the accompanying drawings in which:

FIG. 1 is a simplified illustration of a prior art transducer system;

FIG. 2 is a simplified illustration of the transducer system of the preferred embodiment of the present invention;

DETAILED DESCRIPTION OF THE PREFERRED EMBODIMENT

Figure 3:
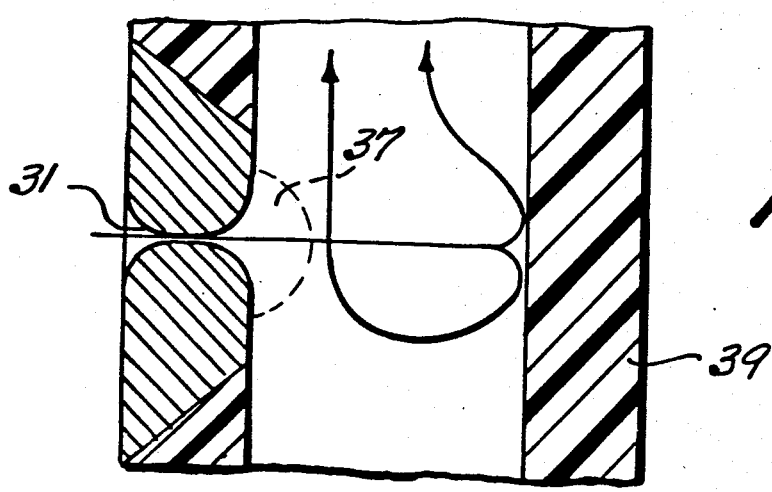
FIG. 3 is a simplified illustration of the fluid flow in the apparatus of the preferred embodiment.
Figure 4:
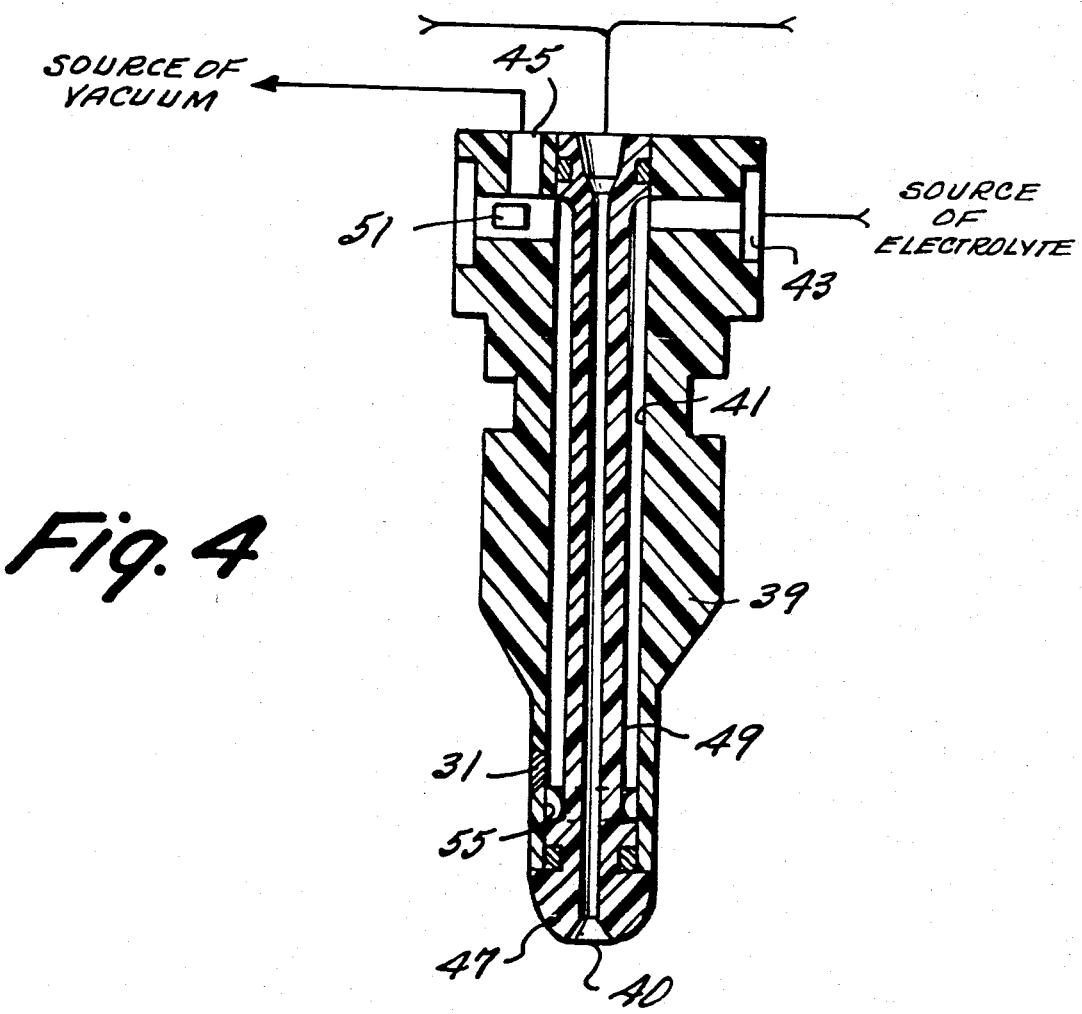
FIG. 4 is a sectional view of the transducer of the preferred embodiment of the present invention.

The preferred embodiment of the invention is illustrated in FIGS. 2-4. With reference to FIG. 2, the transducer is illustrated as having an electrolytic fluid conducting inlet channel 27. The electrolytic fluid which is drawn from a suitable source flows through the channel 27 down to a horizontally disposed transverse channel 29. The fluid is then circulated upwardly in outlet channel 33 past aperture 31 and electrode 35 to a waste container of suitable type. The aperture 31 is formed by shrink fitting a Sapphire ring jewel 32 having a desired aperture size therein onto the transducer as illustrated. As is known in the art, it is substantially easier to form a aperture of the desired small size in, for example, Sapphire, than through a plastic material, such as, polysulfone which forms the transducer.

The flow of electrolyte past the aperture 31 is illustrated schematically in FIG. 3. As illustrated in FIG. 3, a spurious impedance variation region or zone 37 is produced about the downstream side of aperture 31. Thus, any particles reentering this area after having passed through the aperture 31 generates spurious signals which result in an erroneous measurement of the particles being tested. Accordingly, the wall 39 opposite the aperture 31 is positioned sufficiently far from the aperture to permit the particles to flow through the aperture and toward the wall 39 past the spurious signal producing zone. The particles impinge upon the wall and are deflected both above and below the aperture 31. The separation of the wall 39 and the aperture 31 must be large enough so that the flow of electrolyte will remove the particles from the area about the aperture 31 before the particles recirculate into the region 37. The arrows illustrate the trajectory of the particles wherein the particles pass through the orifice 31 and are bounced backwardly from the wall 39 toward the zone 37. As illustrated, the distance between the aperture 31 and the wall 39 is sufficient to permit the particle free electrolytic fluid to transport the particles upwardly and away from the zone 37 before the particles have had a chance to reenter the zone 37.

Referring back to FIG. 2, the particle containing fluid, often termed the sample, is conveyed to a container 38 via a sample inlet channel 40 from a source. After a preselected quantity of the sample has been conducted into the channel 40 and the container 38, a tee valve 42 is operated to conduct air or any other suitable gas to the inlet channel. The air is preferably controllably pulsed through the channel 40 and into the sample fluid in the container 38. The air serves to force any sample fluid in the channel 40 into the container 38 and agitates the sample fluid to insure that it is homogenous throughout.

Refer now to FIG. 4 which is a side section view of the transducer of the preferred embodiment of the present invention. As illustrated, the transducer is preferably formed of two pieces for ease of manufacture. In the preferred embodiment the pieces are formed of a plastic material such as polysulfone. A first outside annular tube member 39 is formed having a cylindrical hollow opening 41 extending the length of the transducer. A fluid inlet orifice 43 is provided through which a particle-free fluid, such as an electrolyte, passes into the transducer. Member 39 also has an outlet orifice 45 through which the particle free electrolytic fluid egresses from the transducer. In order to provide for the measurement of the particles being tested, an electrode 51 is positioned in the path of the electrolyte which electrode is securely fixed to the member 39 by any suitable technique known in the art. As is known, a second electrode positioned in the sample establishes current flow through the aperture 31 for measuring the impedance variance in the aperture caused by particles as they pass therethrough. A second elongated and generally cylindrical member 47 is positioned within the opening 41 in fluid-tight communication with the annular outer member 39. The elongated cylindrical member 47 has grooves formed along the longitudinal axis thereof on diametrically opposite sides of the member. Each of the grooves form, in combination with the outer annular member 39, a fluid conducting channel through which the electrolytic fluid passes. Thus, the electrolytic fluid enters orifice 43, flows through the first groove toward the tip of the transducer where the fluid is conducted into the channel formed by the groove 49. The electrolytic fluid then flows past the electrode 51 and out through the outlet orifice 45.

An aperture 31 of suitable size is located in the outer annular member 39 toward the tip thereof and is in alignment with the groove 49. As aforementioned in connection with the description of FIG. 2, the aperture 31 is formed in a Sapphire jewel. The Sapphire jewel is shrunk fit into the outer annular member 39 by techniques known in the art. The fluid having particles therein is drawn into, and through, the aperture 31 and into the stream of electrolyte flowing past the aperture to thereby force the particles passing through the aperture away from the spurious region proximate the aperture.

As aforementioned, the wall opposite the aperture in the channel is spaced from the aperture so that the particle containing fluid impinges upon the wall and is thereby diffused above and below the aperture. The wall, however, must be sufficiently spaced from the aperture to permit the particles to be transported away from the aperture region before the particles recirculate back into the aperture region. The spacing of the wall from the aperture will vary depending on the size of the aperture, i.e., as the aperture size increases the distance between the wall and aperture will increase. In one example, when blood cells are counted, if the aperture is 50 microns in diameter, the distance between the wall and the aperture is preferably a minimum of 4 millimeters.

it should be understood that the optimum distance between the aperture and wall can be determined by first selecting a distance and then drawing the particle free electrolyte and the particle containing sample through the transducer. The flow rate of the electrolyte should then be decreased toward the desired level until an unacceptable level of spurious impedance variations begins to appear. If this occurs before the desired electrolyte flow level is reached, the wall spacing must be increased. This process is then repeated until the optimum wall spacing is reached.

While the present invention has been disclosed in connection with the preferred embodiment thereof, it should be understood that there may be other embodiments which fall within the spirit and scope of the invention as defined by the appended claims.

What is claimed is:

1. A transducer for measuring particles suspended in a fluid comprising:
    a fluid conducting body member having a fluid conducting channel, said channel having input and output orifices;
    a source of substantially particle-free fluid;
    means for conducting said substantially particle-free fluid from said source, into said input orifice, through said channel, and out from said output orifice;
    an aperture in said fluid conducting member for permitting the ingress of a particle containing fluid into said channel;
    means for measuring the impedance variation of said particle containing fluid in said aperture as said particle containing fluid passes therethrough, said means for measuring being coupled to said fluid conducting channel;
    a container mountable for surrounding at least that portion of said fluid conducting body member that includes said aperture for retaining said particle containing fluid about said aperture;
    a particle containing fluid conducting channel through said fluid conducting member for permitting said particle containing fluid to be conducted therethrough into said container;
    means coupled to at least one of said channels for conducting said particle containing fluid through said particle containing fluid conducting channel into said container; and
    means for controllably forcing a gas into said container through said channel to thereby agitate said particle containing fluid in said container, said agitation maintaining said particle containing fluid homogeneous.

2. A transducer for housing a Coulter-type of measuring aperture for electrically measuring particles in a fluid suspension, wherein the suspended particles are caused to flow through a microscopic aperture-defined path and thereby modify an electrical impedance established in that path, and substantially particle-free fluid is caused to flow proximate the downstream side of the aperture-defined path to sweep particles therefrom, the improvement comprising:
    said transducer having a body with a first and a second channel formed therein for flow therethrough of fluids, each said channel having an inlet orifice and outlet orifice all of which orifices communicate with the exterior of said body;
    said aperture being mounted such that its path is in fluid communication between the exterior of said body, as an input side, and said second channel, as an output side;
    said channels being constructed and arranged such that they are isolated fluidically from each other;
    the exit orifice of said first channel being spaced from the input side of said aperture path and positioned to be in fluid communication with said aperture for supplying thereto the suspension of particles, which is to flow through said first channel; and
    said second channel being adapted to receive particle-free fluid at its input orifice for sweeping past said aperture path output side, for carrying the particles toward said output orifice of said second channel.

3. A transducer according to claim 2 and further including:
    a container mounted with respect to said transducer body so as to receive particles in the fluid suspension from the outlet orifice of said first channel and provide such particles to a location adjacent the input side of said aperture-defined path.

4. A transducer according to claim 3 in which
    said transducer body is oriented such that the outlet orifice of said first channel is below the input side of said aperture-defined path and
    the bottom of said container is positioned below said first channel outlet orifice,
    whereby the fluid suspension first enters said container at a position below said input side of the aperture-defined path.

5. A transducer according to claims 3 or 4 in which said container is mounted such that said inlet and outlet orifices of said second channel are spaced from said container.

6. A transducer according to claims 1 or 2 in which said body is elongate and
    said first channel is formed in said body so as to pass along and through the longitudinal axis thereof.

7. A transducer according to claim 2 in which
    said second channel, at the output side of said aperture-defined path and along a significant distance of said second channel upstream and downstream thereof, has parallel walls so as to not modify the fluid flow velocity along that portion of said second channel.

8. A transducer according to claim 1 in which
    said particle-free fluid conducting channel, at the particle ingress position proximate said aperture and along a significant distance of said channel upstream and downstream thereof, has parallel walls so as to not modify the fluid flow velocity along that portion of said channel.

* * * * *